United States Patent
Patel et al.

(10) Patent No.: US 12,036,199 B1
(45) Date of Patent: Jul. 16, 2024

(54) LEVODOPA FATTY ACID DERIVATIVES, FORMULATIONS THEREOF, AND THEIR USES FOR THE TREATMENT OF PARKINSON'S DISEASE

(71) Applicant: Dynamic Biologics Inc., Monmouth Junction, NJ (US)

(72) Inventors: Deven Patel, Monmouth Junction, NJ (US); Manoj K. Mishra, Monmouth Junction, NJ (US); H. Rajan Sharma, Monmouth Junction, NJ (US); Leema Reddy Peddareddy gari, Monmouth Junction, NJ (US)

(73) Assignee: Dynamic Biologics Inc., Monmouth Junction, NJ (US)

( * ) Notice: Subject to any disclaimer, the term of this patent is extended or adjusted under 35 U.S.C. 154(b) by 0 days.

(21) Appl. No.: 18/218,372

(22) Filed: Jul. 5, 2023

(51) Int. Cl.
*A61K 31/216* (2006.01)
*A61K 31/198* (2006.01)
*A61K 31/277* (2006.01)
*C07C 229/36* (2006.01)

(52) U.S. Cl.
CPC .......... *A61K 31/216* (2013.01); *A61K 31/198* (2013.01); *A61K 31/277* (2013.01); *C07C 229/36* (2013.01)

(58) Field of Classification Search
CPC .. A61K 31/216; A61K 31/198; A61K 31/277; C07C 229/36
See application file for complete search history.

(56) References Cited

U.S. PATENT DOCUMENTS

2006/0025385 A1 * 2/2006 Atlas ............... C07C 237/22
564/163
2016/0002157 A1 * 1/2016 Yu ................... C07C 217/60
548/537

FOREIGN PATENT DOCUMENTS

GB 1347375 * 2/1974

OTHER PUBLICATIONS

Neidhardt, Phys Chem. Chem. Phys. 2018, 20, 20371-81 (Year: 2018).*

* cited by examiner

*Primary Examiner* — Umamaheswari Ramachandran
(74) *Attorney, Agent, or Firm* — Antonio Papageorgiou; Lombard & Geliebter LLP

(57) ABSTRACT

A levodopa derivative including a compound or pharmaceutically acceptable salt, hydrate, and/or solvate thereof, wherein the compound includes substituents which, in aggregate, contain at least 6 carbon atoms which are only bonded to either other carbon atoms or to hydrogen atoms. The levodopa derivative may be formulated as a composition including one or more pharmaceutically acceptable carriers or excipients. The levodopa derivative may be part of a pharmaceutical composition including micro or nano particles in which the levodopa derivative is encapsulated in the pharmaceutically acceptable polymer. The levodopa derivative can be used to treat Parkinson's disease by administering to a mammal an amount sufficient to treat Parkinson's disease.

7 Claims, No Drawings

LEVODOPA FATTY ACID DERIVATIVES, FORMULATIONS THEREOF, AND THEIR USES FOR THE TREATMENT OF PARKINSON'S DISEASE

FIELD OF THE INVENTION

The present invention relates to fatty acid and/or fatty alcohol derivatives of levodopa and polymeric nanoparticle/microparticle formulations of the levodopa derivatives. These compounds and compositions are useful for the treatment of Parkinson's disease.

BACKGROUND OF INVENTION

Levodopa (otherwise referred to as L-DOPA) is the common name for (S)-2-amino-3-(3,4-dihydroxyphenyl)propanoic acid, as shown below:

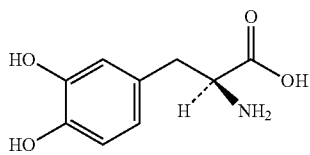 [SMILES: N[C@@H](Cc1ccc(O)c(O)c1)C(=O)O]

Levodopa is an aromatic amino acid derivative which is a main source of dopamine. In human and in other animals, levodopa is synthesized from amino acid L-tyrosine and serves as the precursor in the synthesis of neurotransmitters dopamine, norepinephrine (noradrenaline), and epinephrine (adrenaline), which are collectively known as catecholamines.

Parkinson's disease (PD) is a progressive neurodegenerative disease that affects approximately 1-2% of the population above the age of sixty. Symptoms include resting tremor, rigidity, slowness of movement and postural instability caused by selective degeneration of dopaminergic neurons in the substantia nigra leading to disruption of the nigrostriatal pathway and decreased striatal dopamine levels. Olanow et al., Neurology. 2009; 72(21 Suppl 4):S1-136.

The efficacy of high dose levodopa (3-16 g/day) in treating PD was first reported in 1969 (Cotzias et al., N. Engl. J. Med. 1969; 280(7):337-345; Yahr et al., Arch. Neurol. 1969; 21(4):343-354). The United States Food and Drug Administration ("FDA") approved levodopa for treatment for PD in 1970. Levodopa, unlike dopamine, can cross the blood brain barrier (BBB) and is converted to dopamine in the central nervous system as well as in peripheral circulation (peripheral circulation being circulation prior to crossing the BBB). Most commonly, levodopa is used as a dopamine replacement agent for the treatment of PD and is particularly effective in controlling the bradykinetic symptoms that are apparent in PD. Levodopa is recommended for symptomatic treatment of all stages of Parkinson's disease and is given multiple times every day by oral route. Levodopa is commonly administered with carbidopa, a dopamine decarboxylase inhibitor, to decrease the amount of levodopa that is converted to dopamine in the periphery so more levodopa will cross the BBB to be converted into dopamine. Thus, this combination therapy allows for more levodopa to cross the BBB. Once converted to dopamine, it activates the postsynaptic dopaminergic receptors and compensates for the decrease in endogenous dopamine.

Levodopa is absorbed in the small bowel and 95% of an administered oral dose is pre-systemically decarboxylated to dopamine by the aromatic L-amino acid decarboxylase (AADC) enzyme in the stomach, lumen of the intestine, kidney, and liver. Levodopa may also be methoxylated by the hepatic catechol-O-methyltransferase (COMT) enzyme system to 3-Omethyldopa (3-OMD), which cannot be converted to central dopamine. Therefore, only a small portion of the oral dose of levodopa is transported across the BBB into the central nervous system (CNS) where it is converted to the neurotransmitter dopamine by the brain's AADC enzyme. Dopamine is further converted to sulfated or glucuronidated metabolites, and homovanillic acid through various metabolic processes. The primary metabolites of levodopa are 3,4-dihydroxyphenylacetic acid (13-47%) and homovanillic acid (23-39%).

Because gastric AADC and COMT enzymes degrade levodopa, the drug may be given with: i) a peripheral dopamine decarboxylase inhibitors (carbidopa), without which 90% of levodopa is metabolized in the gut wall, and ii) a COMT inhibitor (entacapone), since COMT inhibitors further improve the bioavailability of levodopa in the brain. See, e.g., Hauser R A. Levodopa: past, present, and future. Eur Neurol. 2009; 62(1):1-8. doi: 10.1159/000215875. Epub 2008 Sep. 9. PMID: 19407449; and Tambasco N, Romoli M, Calabresi P. Levodopa in Parkinson's Disease: Current Status and Future Developments. Curr Neuropharmacol. 2018; 16(8):1239-1252. doi: 10.2174/1570159X15666170510143821. PMID: 28494719; PMCID: PMC6187751.

Inhibitors of AADC and COMT inhibit decarboxylation of levodopa in the stomach and periphery, making more levodopa available for transport across the BBB to increase the dopamine content of the brain. Carbidopa reduces the amount of levodopa required to produce a given response by 75% when administered with levodopa. Co-administered with levodopa/carbidopa, a 200 mg dose of entacapone increases levodopa plasma exposure by 35-40%.

Plasma half-life of levodopa alone is about fifty (50) minutes. When administered along with carbidopa (Sinemet® and Sinemet® CR 50-200), that half-life is increased to 1.5 hours (Sinemet® label, NDA17555). The time to reach peak plasma concentration ($T_{max}$) was about 0.5 hours for Sinemet® and 2 hours for Sinemet® CR, the peak plasma concentration ($C_{max}$) was 1151 ng/mL vs. 3256 ng/mL for Sinemet® vs Sinemet® CR (Sinemet® CR label, NDA 019856). Following administration of Stalevo® (carbidopa, levodopa and entacapone combination, 37.5/150/200 mg), the $t_{max}$ is about 1.5 hours and $C_{max}$ is 1270±329 ng/mL (STALEVO® label, NDA 21485).

Common side effects of levodopa include nausea, vomiting, dry mouth, loss of appetite, heartburn, diarrhea, constipation, dizziness, muscle pain, numbness or tingly feeling and trouble sleeping. Serious side effects include mood changes, increased eye blinking/twitching and worsening of involuntary movements/spasms. Motor fluctuations, including dyskinesia and abnormal involuntary movements, are closely linked to the pharmacokinetics of levodopa, its irregular uptake, short half-life, low bioavailability and marked fluctuations in plasma concentrations. LeWitt, Mov. Disord. 2015; 30(1):64-72; Tambasco et al., Curr Neuropharmacol. 2018; 16(8):1239-1252.

Development of dyskinesia can be avoided by using lower doses of levodopa and by maintaining steady dopamine levels. Research is ongoing to find a delivery route for levodopa to achieve continuous dopaminergic stimulation. An intrajejunal infusion developed by Abbvie (Duopa®) is given by continuous infusion for the treatment of motor fluctuations in patients with advanced Parkinson's disease, and was approved by FDA in 2015. A levodopa inhalation powder, Inbrija® by Acorda Therapeutics, Inc., was approved by the FDA in 2018. Some other formulations for continuous subcutaneous (SC) infusion, such as ABBV-951 (Abbvie) and ND6012 (Neuroderm/Mitsubishi Tanabe) are under development.

Levodopa has been modified to water soluble ester as well as amide derivatives for better brain uptake. See In levodopa, Di Stefano A, Sozio P, Cerasa L S, Iannitelli A. L-Dopa prodrugs: an overview of trends for improving Parkinson's disease treatment. Curr Pharm Des. 2011; 17(32):3482-93. doi: 10.2174/138161211798194495. PMID: 22074421.

In levodopa, there are two benzylic hydroxyl groups at the 3,4-positions of the benzene ring, one amine group at the 2-position of the alkyl chain, and one active carboxyl group at the terminal end of the alkyl chain. The two hydroxyl groups of levodopa can be modified to ester derivatives. The methylester of Levodopa (Levomet®) is already in the market. However, the ethyl ester derivatives (Etilevodopa, TV-1203) were found to be less efficacious than Levodopa in Phase III clinical trials.

WO 2020/264460 discloses a way to decrease the premature reaction of levodopa. The present invention improves upon the invention in WO 2020/264460. The disclosure of WO 2020/264460 is incorporated by reference herein in its entirety.

With current treatments utilizing levodopa (or prodrugs thereof), for the treatment of PD, levodopa has a very short plasma half-life resulting in marked plasma drug concentration fluctuations which in turn results in swings in the amount of levodopa crossing the BBB, resulting in inconsistent levels of dopamine in the brain. As the disease progresses these fluctuations in the plasma concentrations are reflected as swings in the therapeutic response. What is needed is a treatment which will provide steady levels of plasma levodopa concentration resulting in stable quantities crossing the BBB over a longer period. The present invention addresses all those needs.

SUMMARY OF THE INVENTION

In an embodiment, the present invention is directed to a levodopa derivative including a compound or pharmaceutically acceptable salt, hydrate, and/or solvate thereof, wherein the levodopa derivative comprises substituents which, in aggregate, contain at least 6 carbon atoms which are only bonded to either other carbon atoms or to hydrogen atoms. The levodopa derivative may include substituents which, in aggregate, contain 8-100 carbon atoms which are only bonded to either other carbon atoms or to hydrogen atoms.

In an aspect of the invention, the levodopa derivative includes a compound of formula I, or pharmaceutically acceptable salts, hydrates, or solvates thereof,

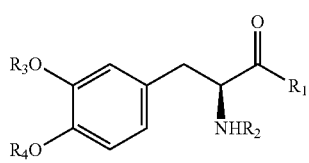

Formula I where $R_1$ may be a C4-34 group, branched or linear, derived from a saturated or unsaturated fatty alcohol, and this C4-34 group directly or indirectly connects to the carbonyl forming an ester, an amide, or an anhydride structure. $R_3$ may be a C4-34 group, branched or linear, derived from a saturated or unsaturated fatty acid, and $R_3$ directly or indirectly connects to the oxygen forming an ester, a carbonate, or a carbamate structure. $R_4$ may be a C4-34 group, branched or linear, derived from a saturated or unsaturated fatty acid, and $R_4$ directly or indirectly connects to the oxygen forming an ester, a carbonate, or a carbamate structure. R2 may be hydrogen, or —(C=O)$R_5$, where $R_5$ may be a $C_{1-3}$ straight or branched chain alkyl group.

In another aspect, the levodopa derivative includes a compound of Formula II, or pharmaceutically acceptable salts, hydrates, or solvates thereof,

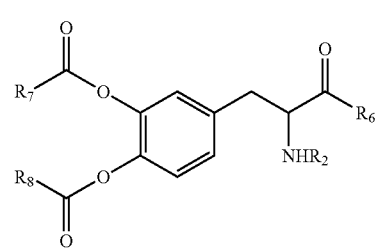

Formula II where $R_6$ may be a derivative of a saturated or unsaturated fatty alcohol, and where $R_7$ may be a derivative of a saturated or unsaturated fatty acid, and wherein $R_8$ may be a derivative of a saturated or unsaturated fatty acid, and where $R_2$ is hydrogen, or —(C=O)$R_5$, where $R_5$ is a $C_{1-3}$ straight or branched chain alkyl group.

In yet another aspect, the levodopa derivative includes a compound of Formula II, or pharmaceutically acceptable salts, hydrates, or solvates thereof,

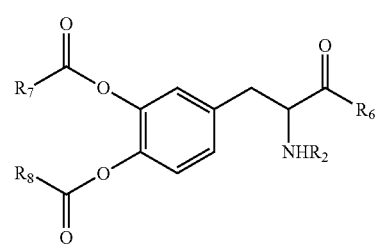

Formula II where $R_6$ may be:
(a) —O—R9, where R-9 may be an alkyl or alkenyl group which may include 4-34 carbon atoms and is branched or linear, substituted or unsubstituted, or
(b) NH—R10, where R10 may be an alkyl or alkenyl group which may include 4-34 carbon atoms and is branched or linear, substituted or unsubstituted, or
(c) —O—C=O—R11, where R11 may be an alkyl or alkenyl group which may include 4-34 carbon atoms and is branched or linear, substituted or unsubstituted, and where R7 may be:
(a) an alkyl or alkenyl group which may include 4-34 carbon atoms and is branched or linear, substituted or unsubstituted, or
(b) —NH—R12, where R12 may be an alkyl or alkenyl group which may include 4-34 carbon atoms and is branched or linear, substituted or unsubstituted, or (c) —O—R13, where R13 includes an alkyl or alkenyl group which may include 4-34 carbon atoms and is branched or linear, substituted or unsubstituted, and where $R_8$ may be
  (a) an alkyl or alkenyl group which may include 4-34 carbon atoms and is branched or linear, substituted or unsubstituted, or
  (b) —NH—R14, where R14 may be an alkyl or alkenyl group which may include 4-34 carbon atoms and is branched or linear, substituted or unsubstituted, or
  (c) —O—R15, where R15 is an alkyl or alkenyl group which may include 4-34 carbon atoms and is branched or linear, substituted or unsubstituted, and
where $R_2$ is hydrogen, or —(C═O)$R_5$, where $R_5$ is a $C_{1-3}$ straight or branched chain alkyl group.

In an aspect of the invention, in Formula II, $R_6$ is selected from the group consisting of: $(CH_3)_3CO$—, $CH_3CH_2C(CH_3)_2O$—, $CH_3CH_2CCH_3(O-)CH_2CH_3$, $CH_3(CH_2)_6O$—, $CH_3(CH_2)_7O$—, $CH_3(CH_2)_8O$—, $CH_3(CH_2)_8CH_2O$—, $CH_3(CH_2)_{10}CH_2O$—, $CH_3(CH_2)_{11}CH_2O$—, $CH_3(CH_2)_{12}CH_2O$—, $CH_3(CH_2)_{13}CH_2O$—, $CH_3(CH_2)_{14}CH_2O$—, $CH_3(CH_2)_5CH═CH(CH_2)_7CH_2O$—, $CH_3(CH_2)_{15}CH_2O$—, $CH_3(CH_2)_{16}CH_2O$—, $CH_3(CH_2)_7$—CH═CH—$(CH_2)_8O$—, $CH_3(CH_2)_{17}CH_2O$—, $CH_3(CH_2)_{18}CH_2O$—, $CH_3(CH_2)_{19}CH_2O$—, $CH_3(CH_2)_{20}CH_2O$—, $CH_3(CH_2)_7CH═CH(CH_2)_{11}CH_2O$—, $CH_3(CH_2)_{22}CH_2O$—, $CH_3(CH_2)_{24}CH_2O$—, $CH_3(CH_2)_{25}CH_2O$—, $CH_3(CH_2)_{26}CH_2O$—, $CH_3(CH_2)_{27}CH_2O$—, $CH_3(CH_2)_{28}CH_2O$—, $CH_3(CH_2)_{30}CH_2O$—, $CH_3(CH_2)_{32}CH_2O$—, $CH_3(CH_2)_3CH═CH(CH_2)_7CH_2O$—, $CH_3(CH_2)_8CH═CH(CH_2)_4CH_2O$—, $CH_3(CH_2)_7CH═CH(CH_2)_7CH_2O$—, $CH_3(CH_2)_5CH═CH(CH_2)_9CH_2O$—, $CH_3(CH_2)_4CH═CHCH_2CH═CH(CH_2)_7CH_2O$—, $CH_3CH_2CH═CHCH_2CH═CHCH_2CH═CH(CH_2)_7CH_2O$—, $CH_3(CH_2)_4CH═CHCH_2CH═CHCH_2CH═CHCH_2CH═CH(CH_2)_3CH_2O$—, $CH_3CH_2CH═CHCH_2CH═CHCH_2CH═CHCH_2CH═CH(CH_2)_3CH_2O$—, $CH_3(CH_2)_7CH═CH(CH_2)_{11}CH_2O$—, and $CH_3CH_2CH═CHCH_2CH═CHCH_2CH═CHCH_2CH═CHCH_2CH═CH(CH_2)_2CH_2O$—.

In Formula II, $R_7$ and/or $R_8$ may be independently selected from the group consisting of: $CH_3(CH_2)_6$—, $CH_3(CH_2)_8$—, $CH_3(CH_2)_{10}$—, $CH_3(CH_2)_{12}$—, $CH_3(CH_2)_{14}$—, $CH_3(CH_2)_{16}$—, $CH_3(CH_2)_{18}$—, $CH_3(CH_2)_{20}$—, $CH_3(CH_2)_{22}$—, $CH_3(CH_2)_{24}$—, $CH_3(CH_2)_3CH═CH(CH_2)_7$—, $CH_3(CH_2)_5CH═CH(CH_2)_7$—, $CH_3(CH_2)_8CH═CH(CH_2)_4$—, $CH_3(CH_2)_7CH═CH(CH_2)_7$—, $CH_3(CH_2)_7CH═CH(CH_2)_7$—, $CH_3(CH_2)_5CH═CH(CH_2)_9$—, $CH_3(CH_2)_4CH═CHCH_2CH═CH(CH_2)_7$-(cis, cis), $CH_3(CH_2)_4CH═CHCH_2CH═CH(CH_2)_7$-(trans, trans), $CH_3CH_2CH═CHCH_2CH═CHCH_2CH═CH(CH_2)_7$—, $CH_3(CH_2)_4CH═CHCH_2CH═CHCH_2CH═CHCH_2CH═CH(CH_2)_3$—, $CH_3CH_2CH═CHCH_2CH═CHCH_2CH═CHCH_2CH═CH(CH_2)_3$—, $CH_3(CH_2)_7CH═CH(CH_2)_{11}$—, and $CH_3CH_2CH═CHCH_2CH═CHCH_2CH═CHCH_2CH═CHCH_2CH═CH(CH_2)_2$—.

In another aspect of the invention, the levodopa derivative may be a compound of formula II, or pharmaceutically acceptable salts, hydrates, or solvates thereof,

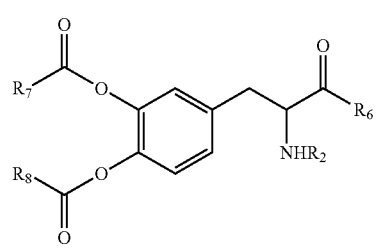

Formula II where $R_6$ may be the following:
  (a) —O—R9, where R-9 may be an alkyl or alkenyl group which includes 4-34 carbon atoms and is branched or linear, substituted or unsubstituted, or
  (b) NH—R10, where R10 may be an alkyl or alkenyl group which includes 4-34 carbon atoms and is branched or linear, substituted or unsubstituted, or
  (c) —O—C═O—R11, where R11 may be an alkyl or alkenyl group which includes 4-34 carbon atoms and is branched or linear, substituted or unsubstituted, and
where R7 may include:
  (a) an alkyl or alkenyl group which includes 4-34 carbon atoms and is branched or linear, substituted or unsubstituted, or
  (b) —NH—R12, where R12 may be an alkyl or alkenyl group which includes 4-34 carbon atoms and is branched or linear, substituted or unsubstituted, or
  (c) —O—R13, where R13 may be an alkyl or alkenyl group which includes 4-34 carbon atoms and is branched or linear, substituted or unsubstituted, and
where R8 may be
  (a) an alkyl or alkenyl group which includes 4-34 carbon atoms and is branched or linear, substituted or unsubstituted, or
  (b) —NH—R14, where R14 may be an alkyl or alkenyl group which includes 4-34 carbon atoms and is branched or linear, substituted or unsubstituted, or
  (c) —O—R15, where R15 may be an alkyl or alkenyl group which includes 4-34 carbon atoms and is branched or linear, substituted or unsubstituted, and
where $R_2$ is hydrogen, or —(C═O)$R_5$, where $R_5$ is a $C_{1-3}$ straight or branched chain alkyl group.

In the present invention, the levodopa derivative may be (S)-4-(2-amino-3-(dodecyloxy)-3-oxopropyl)-1,2-phenylene didodecanoate, which is identified as DB104 in the Examples, with a chemical formula of $C_{45}H_{79}NO_6$, and a molecular weight of 730.13. The levodopa derivative (DB104) may have the following molecular structure.

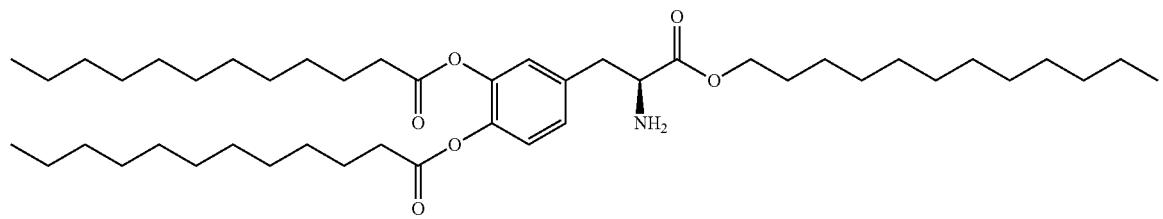

However, levodopa modified with other fatty acids or fatty alcohols is also envisioned in the present invention.

In another aspect, the levodopa derivative is an HCl salt having the following chemical formula:

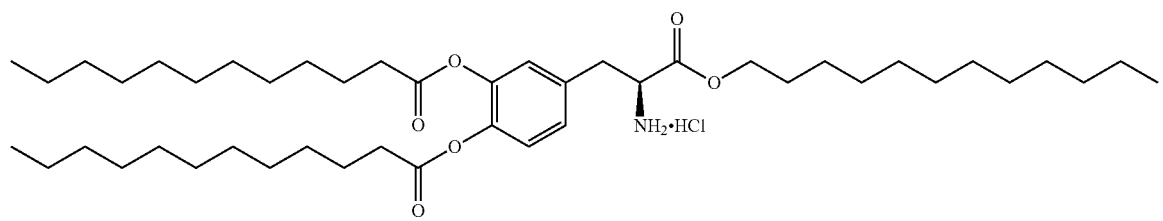

The present invention may be directed to a composition containing a pharmaceutically effective amount of the levodopa derivative of the present invention and one or more pharmaceutically acceptable carriers or excipients. Such composition may be injectable, inhalable, orally ingestible, or topical. Such composition may be in the form of liposomes or micelles. The pharmaceutically acceptable carrier for the levodopa derivative may be castor oil or a derivative thereof.

In yet another embodiment, the present invention may be directed to a pharmaceutical composition containing micro or nano particles including: a pharmaceutically effective amount of the levodopa derivative and a pharmaceutically acceptable polymer, where the levodopa derivative is encapsulated in the pharmaceutically acceptable polymer. The pharmaceutically acceptable polymer may be selected from the group consisting of: polyethylene glycol, poly(glycolide), poly(lactide), poly(caprolactone), poly(lactide-co-caprolactone), poly(lactide-co-glycolide), poly(lactic acid)-butanol, poly(vinyl pyrrolidone), poly(vinyl alcohol), poly(ethyleneimine), poly(malic acid), poly(L-lysine), poly(L-glutamic acid), poly ((N-hydroxyalkyl)glutamine), dextrins, hydroxyethylstarch, polysialic acid, polyacetals, N-(2-hydroxypropyl)methacrylamide copolymer, poly(amido amine) dendrimers, and mixtures, combinations and copolymers thereof.

In yet another aspect, the present invention may be directed to a method for the treatment of Parkinson's disease including administering to a mammal an amount of the levodopa derivative sufficient to treat Parkinson's disease. The levodopa derivative may be in the form of a composition which may be administered intravenously, intramuscularly, intraperitoneally, orally, or subcutaneously.

A composition containing the levodopa derivative may be co-administered with carbidopa and/or entacapone for the treatment of Parkinson's disease.

In another aspect, a composition containing the levodopa derivative may be used to treat Parkinson's by being administered once daily to a Parkinson's patient. In another aspect, the composition may be administered at most twice or thrice weekly. In yet another aspect, the composition may be administered once weekly or biweekly. The composition may be administered once monthly.

In an embodiment, the composition containing the levodopa derivative may be a pharmaceutical composition comprising micro or nano particles containing a pharmaceutically effective amount of the levodopa derivative and a pharmaceutically acceptable polymer, and may be co-administered with carbidopa and/or entacapone to treat Parkinson's disease. Such composition may be administered intravenously, intramuscularly, intraperitoneally, orally, or subcutaneously. Administration may be once daily, at most twice or thrice weekly, once weekly or biweekly, or once monthly.

DETAILED DESCRIPTION

The detailed description set forth below is intended as a description of some, but not all, of the configurations of the subject technology and is not intended to represent an exhaustive list. The detailed description includes specific details for the purpose of providing a thorough understanding of the present invention and subject technology. The subject invention and technology are not limited to the specific details set forth herein and may be practiced without these specific details. In other instances, well-known structures and techniques have not been shown in detail so as not to obscure the disclosure. Exemplary embodiments may be discussed in detail below. While specific exemplary embodiments may be discussed, it should be understood that this would be done for illustration purposes only. In describing and illustrating the exemplary embodiments, specific terminology may be employed for the sake of clarity. However, the embodiments are not intended to be limited to the specific terminology so selected. A person skilled in the relevant art will recognize that other components and configurations may be used without parting from the spirit and scope of the embodiments. It is to be understood that each specific element includes all technical equivalents that operate in a similar manner to accomplish a similar purpose. The examples and embodiments described herein are non-limiting examples.

All publications cited herein are hereby incorporated by reference in their entirety. As used herein, the term "a" refers to one or more. The terms "including," "for example," "such as," "e.g.," "may be" and the like, are meant to include, but not be limited to, the listed examples.

References to "one embodiment," "an embodiment," "example embodiment," "various embodiments," etc., may indicate that the embodiment(s) of the invention so described may include a particular feature, structure, or characteristic, but not every embodiment necessarily includes the particular feature, structure, or characteristic.

Further, repeated use of the phrase "in one embodiment," or "in an illustrative embodiment," do not necessarily refer to the same embodiment, although they may. The various embodiments described herein may be combined and/or features of the embodiments may be combined to form new embodiments.

While various embodiments of the invention have been described herein, it should be understood that this is presented by way of example only, and not limitation. Thus, the breadth and scope of the invention should not be limited by any of the described illustrative embodiments. The embodiments of the invention that are described may contain features that may be removed or combined between the described embodiments to derive additional embodiments. Any range disclosed herein is intended to disclose and discloses any range within such disclosed range.

Headings and subheadings, if any, are used for convenience only and do not limit the invention.

A phrase such as an "aspect" does not imply that such aspect is essential to the subject technology or that such aspect applies to all configurations of the subject technology. A disclosure relating to an aspect may apply to all configurations, or one or more configurations. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. A phrase such an embodiment may refer to one or more embodiments and vice versa.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. Furthermore, to the extent that the term "include," "have," or the like is used in the description or the claims, such term is intended to be inclusive in a manner similar to the term "comprise" as "comprise" is interpreted when employed as a transitional word in a claim.

Levodopa, if utilized by itself to treat Parkinson's, gets greatly degraded before it has an opportunity to cross the BBB and properly result in increased dopamine levels. As part of the present invention, it has been found that by adding "fatty" types of structures as part of a levodopa derivative to protect the levodopa from premature degradation, more levodopa becomes available to cross the BBB. Thus, patients can consume less active ingredient to get better results and this also results in the sustained crossing into the BBB of active ingredient so there are consistent levels of dopamine in the brain.

These "fatty" types of structures assist in protecting the levodopa active portion of the molecule. Furthermore, it is believed that these "fatty" types of structures would be more able to cross the BBB since the structures are more "fatty" and, therefore, soluble in lipids, which is a desired characteristic to cross the BBB. If the "fatty" portion of the molecule is too small, there may be insufficient protection of the levodopa active portion from being prematurely degraded and the levodopa derivative may not be as efficacious in crossing the BBB. Alternatively, if the "fatty" portion is too big, this may make it too difficult to break down the levodopa derivative to usable form and this may also make it more difficult to cross the BBB as easily. The present invention addresses all of those challenges with new chemical structures and compositions as more fully set forth below.

In essence, the compounds of the present invention have several advantages including increased bioavailability at lower doses; predictable drug-release profile over a defined period of time following each administration; better patient compliance; ease of application; improved systemic availability by avoidance of first-pass metabolism; reduced dosing frequency without compromising the effectiveness of the treatment; decreased incidence of side effects; better BBB transfer, and overall cost reduction of medical care.

In an embodiment, the present invention is directed to levodopa derivatives, including certain compounds as well as pharmaceutically acceptable salts, hydrates, and/or solvates of such compounds. The levodopa derivatives, including the compounds as well as pharmaceutically acceptable salts, hydrates, and/or solvates of such compounds, are collectively identified as "Derivatives" or "levodopa derivatives". The Derivatives may include substituents which, in aggregate, contain at least 6 carbon atoms which are only bonded to either other carbon atoms or to hydrogen atoms. This is some of the "fatty" part of the molecules in the present invention. The Derivatives may include substituents which, in aggregate, contain 8-100 carbon atoms which are only bonded to either other carbon atoms or to hydrogen atoms. In other embodiments, the number of carbons which are only bonded to either other carbon atoms or to hydrogen atoms is 15-90, 25-80, 30-50, 32-40, and any ranges within these ranges, such as any range between 8-100 carbon atoms are envisioned in the present invention. Since the present invention seeks to add "fatty" protecting groups to levodopa, the Derivatives may be synthesized with the use of fatty acids and fatty alcohols, and this will be explained further below. Also, additional specifics on what types of molecules may be part of the Derivatives will also be described.

Masking one or both reactive hydroxyl groups in the phenyl ring and/or the carboxylic acid group of levodopa with fatty type of structures is one way to implement the present invention. The amine group of levodopa can also be masked. Fatty acid derivatives can be reacted with the hydroxyl groups in the phenyl ring of levodopa in order to add the "fatty" type of structure to the molecule. The carboxylic acid group in levodopa can be reacted with a fatty alcohol derivatives to add more of such "fatty" type of structure. The fatty groups can, for example, be bonded to the hydroxyl groups or the carbonyl groups with the formation of ester groups. These ester groups contain in vivo cleavable bonds so they can be reacted within the body to eventually end up with free levodopa, since free levodopa is needed to produce dopamine. The amine in levodopa can also be reacted with once it has been masked to result in free levodopa. The masking of the present invention also reduces the chances of peripheral degradation of levodopa to dopamine by AADC and COMT enzymes, thereby increasing the subsequent availability of levodopa in the brain. The Derivatives provide sustained plasma levels of levodopa with increased delivery of levodopa to the brain, resulting in improved efficacy.

In an aspect of the invention, the Derivatives include a compound of formula I, or pharmaceutically acceptable salts, hydrates, and/or solvates thereof,

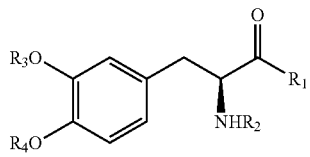

Formula I where $R_1$ may be a C4-34 group, branched or linear, derived from a saturated or unsaturated fatty alcohol, and this C4-34 group directly or indirectly connects to the carbonyl forming an ester, an amide, or an anhydride structure. $R_3$ may be a C4-34 group, branched or linear, derived from a saturated or unsaturated fatty acid, and $R_3$ directly or indirectly connects to the oxygen forming an ester, a carbonate, or a carbamate structure. $R_4$ may be a C4-34 group, branched or linear, derived from a saturated or unsaturated fatty acid, and $R_4$ directly or indirectly connects to the oxygen forming an ester, a carbonate, or a carbamate structure. $R_2$ may be hydrogen, or $-(C=O)R_5$, where $R_5$ may be a $C_{1-3}$ straight or branched chain alkyl group, which can be substituted or unsubstituted. The number of carbons identified above for R1, R3 and R4 is 4-34, however, various other ranges are also possible. Other ranges can include C4-C26, C6-C30, C8-C25, C10-C20, and C11-C15, and C12. All ranges within the range of C4-34 are also envisioned. The number of carbon atoms for R1, R3, and R4 may be the same or different.

In another aspect, the Derivatives include a compound of Formula II, or pharmaceutically acceptable salts, hydrates, or solvates thereof,

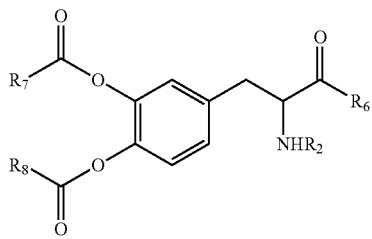

Formula II where $R_6$ may be a derivative of a saturated or unsaturated fatty alcohol, and
where R7 may be a derivative of a saturated or unsaturated fatty acid, and
wherein $R_8$ may be a derivative of a saturated or unsaturated fatty acid, and where
$R_2$ is hydrogen, or $-(C=O)R_5$, where $R_5$ is a $C_{1-3}$ straight or branched chain alkyl group, substituted or unsubstituted.

In yet another aspect, the Derivatives include a compound of Formula II, or pharmaceutically acceptable salts, hydrates, or solvates thereof,

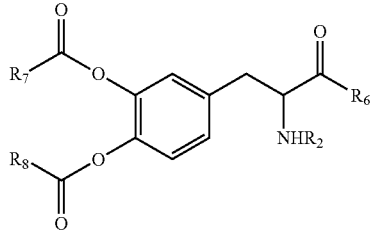

Formula II where $R_6$ may be:
(a) —O—R9, where R-9 may be an alkyl or alkenyl group which may include 4-34 carbon atoms and is branched or linear, substituted or unsubstituted, or
(b) NH—R10, where R10 may be an alkyl or alkenyl group which may include 4-34 carbon atoms and is branched or linear, substituted or unsubstituted, or
(c) —O—C=O—R11, where R11 may be an alkyl or alkenyl group which may include 4-34 carbon atoms and is branched or linear, substituted or unsubstituted,
and where R7 may be:
(a) an alkyl or alkenyl group which may include 4-34 carbon atoms and is branched or linear, substituted or unsubstituted, or
(b) —NH—R12, where R12 may be an alkyl or alkenyl group which may include 4-34 carbon atoms and is branched or linear, substituted or unsubstituted, or
(c) —O—R13, where R13 may be an alkyl or alkenyl group which may include 4-34 carbon atoms and is branched or linear, substituted or unsubstituted, and
where $R_8$ may be
(a) an alkyl or alkenyl group which may include 4-34 carbon atoms and is branched or linear, substituted or unsubstituted, or
(b) —NH—R14, where R14 may be an alkyl or alkenyl group which may include 4-34 carbon atoms and is branched or linear, substituted or unsubstituted, or
(c) —O—R15, where R15 is an alkyl or alkenyl group which may include 4-34 carbon atoms and is branched or linear, substituted or unsubstituted, and
where $R_2$ is hydrogen, or $-(C=O)R_5$, where $R_5$ is a $C_{1-3}$ straight or branched chain alkyl group, and it may be substituted or unsubstituted.

R9, R10, R11, R12, R13, R14, and R15 may, independently, contain 4-34 carbon atoms. However, they can, independently, contain other ranges of carbon atoms. Other ranges can include $C_6$-C30, $C_8$-C25, C10-C20, and C11-C15, and C12. All ranges within the range of C4-34 are also envisioned. The number of carbon atoms for R9, R10, R11, R12, R13, R14, and R15 may be the same or different.

In an aspect of the invention, R6 in Formula II is selected from the group consisting of: $(CH_3)_3CO-$, $CH_3CH_2C(CH_3)_2O-$, $CH_3CH_2CCH_3(O-)CH_2CH_3$, $CH_3(CH_2)_6O-$, $CH_3(CH_2)_7O-$, $CH_3(CH_2)_8O-$, $CH_3(CH_2)_8CH_2O-$, $CH_3(CH_2)_{10}CH_2O-$, $CH_3(CH_2)_{11}CH_2O-$, $CH_3(CH_2)_{12}CH_2O-$, $CH_3(CH_2)_{13}CH_2O-$, $CH_3(CH_2)_{14}CH_2O-$, $CH_3(CH_2)_5CH=CH(CH_2)_7CH_2O-$, $CH_3(CH_2)_{15}CH_2O-$, $CH_3(CH_2)_{16}CH_2O-$, $CH_3(CH_2)_7CH=CH(CH_2)_8O-$, $CH_3(CH_2)_{17}CH_2O-$, $CH_3(CH_2)_{18}CH_2O-$, $CH_3(CH_2)_{19}CH_2O-$, $CH_3(CH_2)_{20}CH_2O-$, $CH_3$ (CH$_2$)$_7$CH=CH(CH$_2$)$_{11}$CH$_2$O—, CH$_3$(CH$_2$)$_{22}$CH$_2$O—, CH$_3$(CH$_2$)$_{24}$CH$_2$O—, CH$_3$(CH$_2$)$_{25}$CH$_2$O—, CH$_3$(CH$_2$)$_{26}$CH$_2$O—, CH$_3$(CH$_2$)$_{27}$CH$_2$O—, CH$_3$(CH$_2$)$_{28}$CH$_2$O—, CH$_3$(CH$_2$)$_{30}$CH$_2$O—, CH$_3$(CH$_2$)$_{32}$CH$_2$O—, CH$_3$(CH$_2$)$_3$CH=CH(CH$_2$)$_7$CH$_2$O—, CH$_3$(CH$_2$)$_5$CH=CH(CH$_2$)$_4$CH$_2$O—, CH$_3$(CH$_2$)$_7$CH=CH(CH$_2$)$_7$CH$_2$O—, CH$_3$(CH$_2$)$_5$CH=CH(CH$_2$)$_9$CH$_2$O—, CH$_3$(CH$_2$)$_4$CH=CHCH$_2$CH=CH(CH$_2$)$_7$CH$_2$O—, CH$_3$CH$_2$CH=CHCH$_2$CH=CHCH$_2$CH=CH(CH$_2$)$_7$CH$_2$O—, CH$_3$(CH$_2$)$_4$CH=CHCH$_2$CH=CHCH$_2$CH=CHCH$_2$CH=CH(CH$_2$)$_3$CH$_2$O—, CH$_3$CH$_2$CH=CHCH$_2$CH=CHCH$_2$CH=CHCH$_2$CH=CH(CH$_2$)$_3$CH$_2$O—, CH$_3$(CH$_2$)$_7$CH=CH(CH$_2$)$_{11}$CH$_2$O—, and CH$_3$CH$_2$CH=CHCH$_2$CH=CHCH$_2$CH=CHCH$_2$CH=CHCH$_2$CH=CH(CH$_2$)$_2$CH$_2$O—.

In Formula II, $R_7$ and/or $R_8$ may be independently selected from the group consisting of: CH$_3$(CH$_2$)$_6$—, CH$_3$(CH$_2$)$_8$—, CH$_3$(CH$_2$)$_{10}$—, CH$_3$(CH$_2$)$_{12}$—, CH$_3$(CH$_2$)$_{14}$—, CH$_3$(CH$_2$)$_{16}$—, CH$_3$(CH$_2$)$_{18}$—, CH$_3$(CH$_2$)$_{20}$—, CH$_3$(CH$_2$)$_{22}$—, CH$_3$(CH$_2$)$_{24}$—, CH$_3$(CH$_2$)$_3$CH=CH(CH$_2$)$_7$—, CH$_3$(CH$_2$)$_5$CH=CH(CH$_2$)$_7$—, CH$_3$(CH$_2$)$_8$CH=CH(CH$_2$)$_4$—, CH$_3$(CH$_2$)$_7$CH=CH(CH$_2$)$_7$—, CH$_3$(CH$_2$)$_7$CH=CH(CH$_2$)$_7$—, CH$_3$(CH$_2$)$_5$CH=CH(CH$_2$)$_9$—, CH$_3$(CH$_2$)$_4$CH=CHCH$_2$CH=CH(CH$_2$)$_7$-(cis, cis), CH$_3$(CH$_2$)$_4$CH=CHCH$_2$CH=CH(CH$_2$)$_7$-(trans, trans), CH$_3$CH$_2$CH=CHCH$_2$CH=CHCH$_2$CH=CH(CH$_2$)$_7$—, CH$_3$(CH$_2$)$_4$CH=CHCH$_2$CH=CHCH$_2$CH=CHCH$_2$CH=CH(CH$_2$)$_3$—, CH$_3$CH$_2$CH=CHCH$_2$CH=CHCH$_2$CH=CHCH$_2$CH=CHCH$_2$CH=CH(CH$_2$)$_3$—, CH$_3$(CH$_2$)$_7$CH=CH(CH$_2$)$_{11}$—, and CH$_3$CH$_2$CH=CHCH$_2$CH=CHCH$_2$CH=CHCH$_2$CH=CHCH$_2$CH=CH(CH$_2$)$_2$—.

One way to make the structure of Formula II is to react levodopa or a derivative thereof directly with a fatty alcohol(s) or fatty acid(s). Another way is to first derivatize the fatty alcohol(s) or fatty acid(s) with another functional group (such as an amine functionality), and this can then be reacted with levodopa or a derivative thereof. For example, if a fatty alcohol is derivatized with an amine functionality and then the fatty alcohol is reacted with the carbonyl group on the right side of Formula II, then R6 can be NH—R10, as explained above.

In the present invention, the levodopa derivative may be (S)-4-(2-amino-3-(dodecyloxy)-3-oxopropyl)-1,2-phenylene didodecanoate, which is also identified as DB104 in the Examples below. The chemical formula is C$_{45}$H$_{79}$NO$_6$, and it has a molecular weight of 730.13. The levodopa derivative (DB104) may have the following molecular structure.

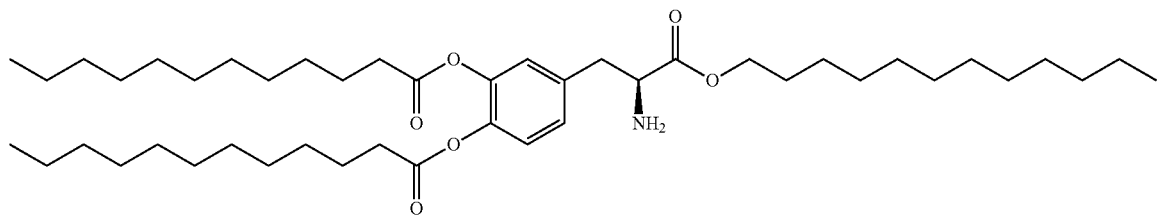 [SMILES: CCCCCCCCCCCCOC(=O)[C@@H](N)Cc1ccc(OC(=O)CCCCCCCCCCC)c(OC(=O)CCCCCCCCCCC)c1]

In another aspect, the levodopa derivative is an HCl salt having the following chemical formula:

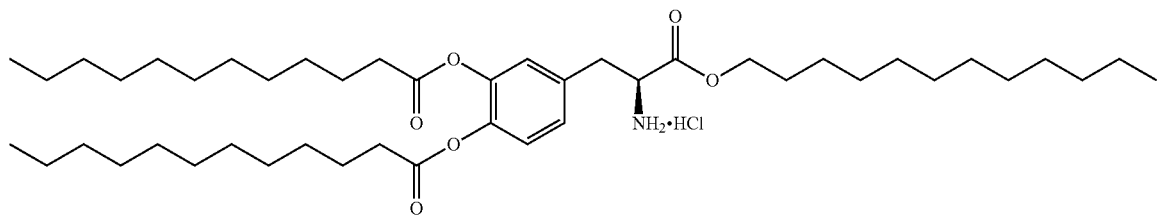

The present invention may be directed to a composition containing a pharmaceutically effective amount of one or more Derivatives of the present invention and one or more pharmaceutically acceptable carriers or excipients. Such composition may be injectable, inhalable, orally ingestible, or topical. Such composition may be in the form of liposomes or micelles. The pharmaceutically acceptable carrier for the one or more Derivatives may be castor oil or a derivative thereof. Various carriers and excipients are known in the art as well as ways to make compositions injectable, inhalable, orally ingestible, or topical. The formation of liposomes or micelles is also known in the pharmaceutical arts. Accordingly, further elaboration is not needed.

In some embodiments, dosage forms of the composition of the invention are adapted for administration to a patient parenterally, including subcutaneous, intramuscular, intraperitoneal, intravenous or intradermal injections. In other embodiments, the composition may be administered as a depot. Upon parenteral injection of the Derivatives, enzymatic cleavage may occur generating levodopa.

In yet another embodiment, the present invention may be directed to a pharmaceutical composition comprising micro or nano particles comprising: a pharmaceutically effective amount of one or more of the Derivatives and a pharmaceutically acceptable polymer, where the one or more of the Derivatives are encapsulated in the pharmaceutically acceptable polymer. The pharmaceutically acceptable polymer may be selected from the group consisting of: polyethylene glycol, poly(glycolide), poly(lactide), poly(caprolactone), poly(lactide-co-caprolactone), poly(lactide-co-glycolide), poly(lactic acid)-butanol, poly(vinyl pyrrolidone), poly(vinyl alcohol), poly(ethyleneimine), poly(malic acid), poly(L-lysine), poly(L-glutamic acid), poly ((N-hydroxyalkyl)glutamine), dextrins, hydroxyethylstarch, polysialic acid, polyacetals, N-(2-hydroxypropyl)methacrylamide copolymer, poly(amido amine) dendrimers, and mixtures, combinations and copolymers thereof. These polymers are known in the art and further elaboration is not necessary. In some embodiments, poly(lactide-co-glycolide) (PLGA) and a mixture of PLGA with other polymers, such as poly(lactide) (PLA), polyglycolide (PGA) and polyvinyl alcohol (PVA), in different ratios are used to encapsulate compounds of the invention to form microparticles or nanoparticles. Due to its excellent biocompatibility, PLGA is a pharmaceutically acceptable biodegradable polymer widely used for encapsulation of a broad range of therapeutic agents including hydrophilic and hydrophobic small molecule drugs, DNA, and proteins. Other additives can be used to enhance the drug loading and efficiency in PLGA microparticles, such as polyethylene glycol (PEG), poly(orthoesters), chitosan, alginate, caffeic acid, hyaluronic acid etc. PLGA can be a varying composition of PLA and PGA with a ratio from 20 to 80% PGA in PLA and vice versa, and any ranges within these ranges.

Polymer-encapsulated micro/nano particles may be prepared by methods known in the art. See, for example, Han et al., Front Pharmacol. 2016; 7:185; Qutachi et al., Acta Biomater. 2014; 10(12):5090-5098. Preparation of microparticles of Derivatives can be done as follows. Nanoprecipitation technique may be used for the preparation of the levodopa microparticles. Briefly, Derivatives and a polymer (e.g., PLGA) are dissolved in a suitable solvent (e.g., dichloromethane) in different ratios, the mixture being subjected to sonication for 5-10 minutes to achieve dissolution, if required. Dissolution of a hydrophilic non-ionic surfactant (for example a triblock copolymer), such as Pluronic F127, in 50 mL of deionized water may be carried out and adding the Derivatives/PLGA solution dropwise using a syringe with a flow rate of 1 mL/10 min with stirring at varying speed may be done as well. Centrifugation, and lyophilization of the obtained nanosuspension with cryoprotectant (e.g., 2% sucrose) can be done. Characterization of the resulting particles with scanning electron microscopy (SEM), differential scanning calorimetry (DSC) and X-Ray diffraction (XRD) can be done.

The term "encapsulated" in the context of the present invention means coated by, covered by, or surrounded by, such that a least about 20% of the Derivatives are enclosed/covered/coated by the polymer. Preferably, about 20% to about 80% of the Derivatives are enclosed/covered/coated. The enclosure does not have to be a complete surrounding of the Derivatives but it should be at least 30%. Thus, preferably, are least about 20% of the Derivatives which are in the form of micro/nano particles would be covered, and such coverage would be at least 30% of the surface. Preferably, up to 80% of the surface would be covered although coverage of 100% of the surface is also possible at least with some of the particles.

A pharmaceutical composition which contains one or more of the Derivatives may further include one or more pharmaceutically acceptable carriers or excipients. Such composition, as stated above, may be injectable, inhalable, orally ingestible, or topical. Pharmaceutical compositions adapted for parenteral administration include aqueous and non-aqueous sterile injection solutions which may contain anti-oxidants, buffers, bacteriostats, and solutes that render the formulation isotonic with the blood of the intended recipient; and aqueous and non-aqueous sterile suspensions which may include suspending agents and thickening agents. The compositions may be presented in unit-dose or multi-dose containers, for example, sealed ampules and vials.

The compositions may be presented in unit-dose or multi-dose containers, for example, sealed ampules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

In yet another aspect, the present invention may be directed to a method for the treatment of Parkinson's disease including administering to a mammal an amount of one or more of the Derivatives sufficient to treat Parkinson's disease. The one or more Derivatives may be in the form of a composition which may be administered intravenously, intramuscularly, intraperitoneally, orally, or subcutaneously.

A composition containing one or more of the Derivatives may be co-administered with carbidopa and/or entacapone for the treatment of Parkinson's disease. As stated above, carbidopa helps to reduce the premature degradation of levodopa so even if the Derivatives of the present invention were to lose some of the "fatty" portions, the carbidopa can still help reduce the amount of active ingredient which is degraded and is not available for formation of dopamine.

In some embodiments, the amount of compound of Derivatives in the compositions of the invention is in the range of 100 mg to 2000 mg equivalent of levodopa administered once daily. Compositions comprising 10-200 mg of carbidopa and/or 200-1600 mg of entacapone (or other COMT inhibitors) may be used in combination with the compositions of the invention for treatment of PD. Thus, compositions of the invention may include carbidopa and/or entacapone in addition to the compound of the Derivatives. The amount of carbidopa co-administered with Derivatives may be in a ratio of 1:10 to 1:4 with respect to the amount of Derivatives and/or the amount of equivalent levodopa in the Derivatives. COMT inhibitors, such as tolcapone, opicapone, and/or entacapone may be co-administered with Derivatives in a dose of 200 mg or more and the dosage repeated as required, and carbidopa may or may not be co-administered as well. Carbidopa in an amount of 10 mg to 200 mg/day and/or entacapone (or another COMT inhibitor) in an amount of 200 mg to 1600 mg/day may be co-administered with the compounds or compositions of the invention.

In another aspect, a composition containing one or more of the Derivatives may be used to treat Parkinson's by being administered once daily to a Parkinson's patient. In another aspect, the composition may be administered at most twice or thrice weekly. In yet another aspect, the composition may be administered once weekly or biweekly. The composition may be administered once monthly.

In an embodiment, the composition containing one or more of the Derivatives may be a pharmaceutical composition comprising micro or nano particles containing a pharmaceutically effective amount of one or more of the Derivatives and a pharmaceutically acceptable polymer, and may be co-administered with carbidopa and/or entacapone (or other COMT inhibitors) to treat Parkinson's disease. Such composition may be administered intravenously, intramuscularly, intraperitoneally, orally, or subcutaneously. Administration may be once daily, at most twice or thrice weekly, once weekly or biweekly, or once monthly.

Example 1 below demonstrates that the Derivatives of the present invention result in protection of the active ingredient so that there is less early degradation of levodopa, resulting in more of it being available to form into dopamine after crossing the BBB.

Example 1

10 μM DB104 (DB104 is identified above and is one of the Derivatives of the present invention) was incubated in fresh plasma and phosphate buffer saline (PBS) in multiple aliquots, and each aliquot was divided into two equal halves at the following time points: 0, 1, 2, 4, 6, 24, 48, 72, 96, 120, 144, 168, 192, 216, 240, and 264 h. The first half was quenched with ACN:MeOH containing 1% formic acid and analyzed on the high-resolution mass spectroscopy (HRMS) to detect DB104 and all other possible intermediates. Labetalol was used as internal standard (IS). The other half was quenched with perchloric acid and analyzed on an AB Sciex 7500 mass spectrometer to detect L-DOPA. Dopamine-d4 will be used as IS.

Possible intermediates structures from the steps above are as follows:

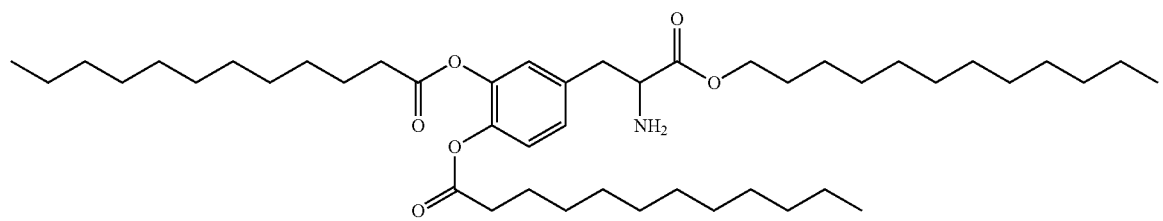

DB104

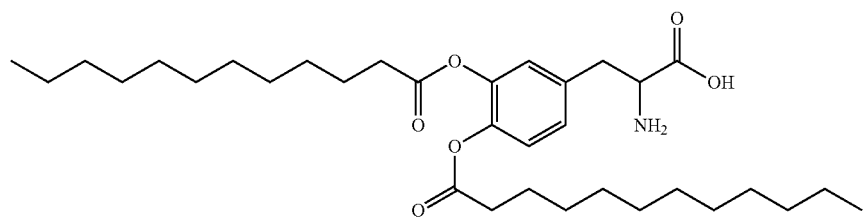

DB104M1

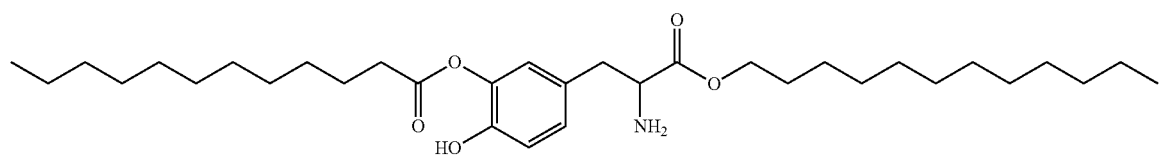

DB104M4

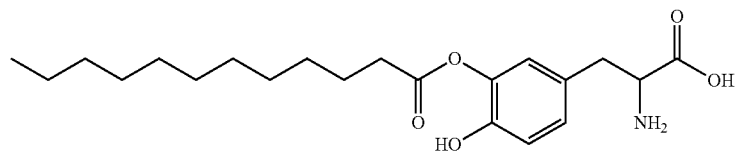

DB104M2

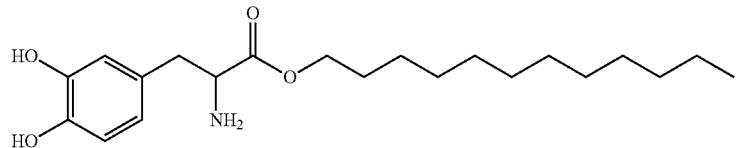

DB104M3

L-DOPA

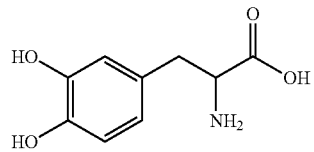

DB104 took about 4 h and 1-4 h to get fully solubilized in human plasma and PBS, respectively. This was evident by initial increase in peak area followed by degradation. All peak area ratios were normalized to the max peak area ratio value observed. DB104M3 and DB104M4, and L-DOPA were observed in human plasma and PBS. DB104M1 was observed in PBS only. DB104M2 was not observed in either human plasma or PBS. In vitro half-life of DB104 in human plasma was 13.1±1.4 hours, which is significant. In vitro half-life of DB104 in PBS was 12.4±2.6 hr, which is also significant.

The testing described above resulted in a vitro half-life of DB104 estimated at 12 h in both human plasma and PBS. L-DOPA is formed at detectable amounts for up to 72 h in both human plasma and PBS, which demonstrated less periphery degradation and more L-DOPA available to cross the BBB. DB104M4 was the major degradant in PBS. It is hypothesized that DB104 may also cross the BBB and that the L-DOPA may be formed after crossing of the BBB by the Derivatives.

The Derivatives can be produced by using fatty acids and fatty alcohols. For example, in Formula II above, R6 could be made by using fatty alcohols and R7 and R8 could be made by using fatty acids.

Fatty alcohols which may be used to make a derivative of levodopa include, but are not limited to, the following: tert-Butyl alcohol, tert-Amyl alcohol, 3-Methyl-3-pentanol, 1-Heptanol (enanthic alcohol), 1-Octanol (capryl alcohol), Pelargonic alcohol (1-nonanol), 1-Decanol (decyl alcohol, capric alcohol), Undecyl alcohol (1-undecanol, undecanol, Hendecanol), Lauryl alcohol (dodecanol, 1-dodecanol), Tridecyl alcohol (1-tridecanol, tridecanol, isotridecanol), Myristyl alcohol (1-tetradecanol), Pentadecyl alcohol (1-pentadecanol, pentadecanol), Cetyl alcohol (1-hexadecanol), Palmitoleyl alcohol (cis-9-hexadecen-1-ol), Heptadecyl alcohol (1-n-heptadecanol, heptadecanol), Stearyl alcohol (1-octadecanol), Oleyl alcohol (1-octadecenol), Nonadecyl alcohol (1-nonadecanol), Arachidyl alcohol (1-eicosanol), Heneicosyl alcohol (1-heneicosanol), Behenyl alcohol (1-docosanol), Erucyl alcohol (cis-13-docosen-1-ol), Lignoceryl alcohol (1-tetracosanol), Ceryl alcohol (1-hexacosanol), 1-Heptacosanol, Montanyl alcohol, cluytyl alcohol, or 1-octacosanol, 1-Nonacosanol, Myricyl alcohol, melissyl alcohol, or 1-triacontanol, 1-Dotriacontanol (Lacceryl alcohol), Geddyl alcohol (1-tetratriacontanol), trans-9-Octadecenol, and cis,cis-9,12-Octadecadien-1-ol. Other fatty alcohols can also be used.

Fatty acids which may be used to make a derivative of levodopa include, but are not limited to, the following: Caprylic acid, Capric acid, Lauric acid, Myristic acid, Palmitic acid, Stearic acid, Arachidic acid, Behenic acid, Lignoceric acid, Cerotic acid, Myristoleic acid, Palmitoleic acid, Sapienic acid, Oleic acid, Elaidic acid, Vaccenic acid, Linoleic acid, Linoelaidic acid, α-Linolenic acid, Arachidonic acid, Eicosapentaenoic acid, Erucic acid, Docosahexaenoic acid. Other fatty acids can also be used.

Example 2 below shows the use of levodopa to form a particular example of the Derivatives according to the present invention.

Example 2

Preparation of Di-Lauroxil Levodopa Dodecylester HCl Salt:

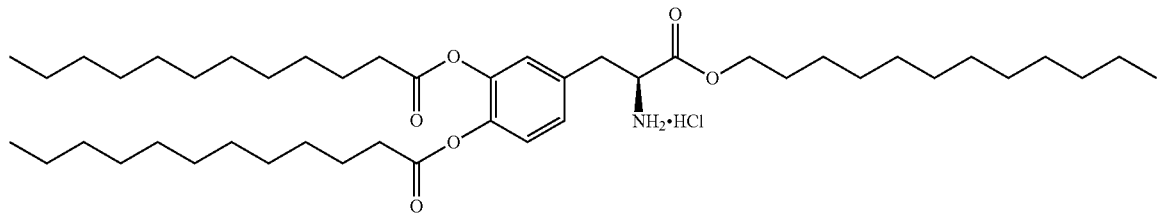

Experimental Procedure:

Preparation of N-(tert-butyloxycarbonyl)-3,4-dihydroxy-L-phenylalaine (Boc-Levodopa): Levodopa (25 gm, 0.126 mol) was stirred in a mixture of dioxane (150 mL), water (100 mL), 1M NaOH (100 mL) under nitrogen atmosphere for 30 min at room temperature. Tert-butyl dicarbonate (35 gm, 0.160 mol) was added slowly at room temperature and the reaction is stirred for 20 hrs. After the completion of the reaction, the solvent was evaporated under vacuum to reduce the volume to half. The organic materials were extracted using ethyl acetate (3×100 mL). The combined organic layer was washed with water (100 mL) followed by brine (50 mL) and the final organic layer was dried over anhydrous $Na_2SO_4$. The organic layer was concentrated under vacuum at a temperature below 55° C. to obtain a brown foamy solid. The obtained crude product was purified by column chromatography on silica gel (100-200 mesh) using Dichloromethane & Methanol (6:4) as eluent system to get the Boc-Levodopa (yield: 10.5 gm, 30%).

Preparation of Boc-Levodopa-dodecylester: Boc-Levodopa (20 gm) was stirred with DMF (100 mL) under nitrogen atmosphere in a round bottom flask at room temperature. $Na_2CO_3$ was added to the reaction mixture followed by 1-Bromododecane (which can be derived from the fatty alcohol dodecanol) and was stirred for 16 hrs to complete the reaction. The reaction mixture was filtered and the filtrate was concentrated under vacuum at below 55° C. to remove the solvent completely. Water (100 mL) was added to the residue and the pH was adjusted to acidic side using 6N HCl (8.3 mL) and the organic mixture was extracted with ethyl acetate (2×100 mL). The combined organic layer was washed with water (50 mL) followed by brine (50 mL) and dried over anhydrous Na$_2$SO$_4$. Finally organic layer was concentrated under vacuum to get a brown thick liquid. The obtained residue was purified by column chromatography using ethyl acetate and n-hexane mixture (6:4) to get the pure product (Yield: 9.2 gm, 28%).

Preparation of Di-lauroxil-Boc-Levodopa dodecyl Ester: Boc-Levodopa-dodecylester (8.5 gm) was stirred with DCM (10 mL) in a round bottom flask under nitrogen at room temperature. The reaction mixture was cooled in an ice bath by maintaining temp between 0-5° C. Lauroyl chloride (2.85 gm) in DCM (15 mL) was added drop wise to the reaction mixture. Lauroyls chloride is the acid chloride of lauric acid, which is a fatty acid. After stirring for 10 min, the reaction mixture was stirred at room temperature to complete the reaction. The reaction mass was washed with DI water (4×50 mL) and the organic layer was dried over anhydrous Na$_2$SO$_4$. The obtained DCM layer was concentrated under vacuum to obtain an orange thick residue. The residue was purified by column chromatography using ethyl acetate and n-hexane mixture (6:4) as eluent to obtain the pure product (Yield: 2.75 gm, 19%).

Preparation of Di-lauroxil-Levodopa-dodecylester HCl salt: A mixture of Di-lauroxil-Boc-Levodopa-dodecylester (2.5 gm) and HCl/Dioxane (2N, 80 mL) were stirred at 25-30° C. for 2-3 hours. After completion of reaction, solvent was completely removed at 30-35° C. under vacuum. The obtained residue which was an HCl salt, was further stirred in fresh Dioxane (25 mL) at 25-30° C. for 2 hr. The solid was filtered and dried under vacuum in a desiccator for 8-10 hrs to get the pure target product (Yield: 1.6 gm, 62%). HPLC Purity: 98.69; Mass (M+1): 730.59; $^1$H-NMR (DMSO-d$_6$): δ 0.83-0.86 (9H, t, —CH$_3$), 1.10-1.40 (52H, m, CH$_2$ aliphatic protons), 1.58-1.61 (4H, m, CH$_2$ aliphatic protons), 2.50-2.54 (4H, m, CH$_2$—CO), 3.00 (1H, dd, benzylic CH$_2$), 3.20 (1H, dd, benzylic CH$_2$), 3.98-4.01 (2H, m, OCH$_2$), 4.27-4.30 (1H, m, CH—NH), 7.13-7.22 (3H, m, aromatic protons), 8.55 (3H, broad Singlet, NH protons). Thus, the Di-lauroxil-levodopa-dodecylester HCl salt product was produced and can be utilized to treat Parkinson's. Different fatty alcohols and fatty acids can be used instead of the ones that were used above in order to have different chains reacted as part of the Derivatives.

What is claimed:

1. A compound of Formula II, or a pharmaceutically acceptable salt, hydrate, or solvate thereof,

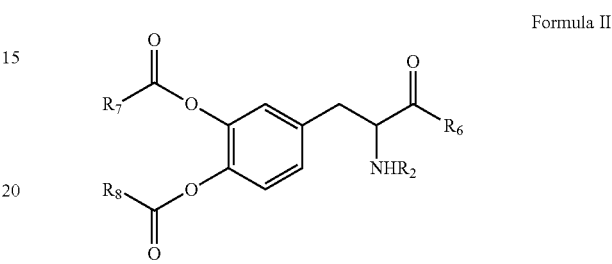

Formula II wherein R$_2$ is H,
wherein R$_6$ is CH$_3$(CH$_2$)$_{10}$CH$_2$O—, and
wherein R$_7$ and R$_8$ are CH$_3$(CH$_2$)$_{10}$.

2. The compound according to claim 1, wherein the compound is:

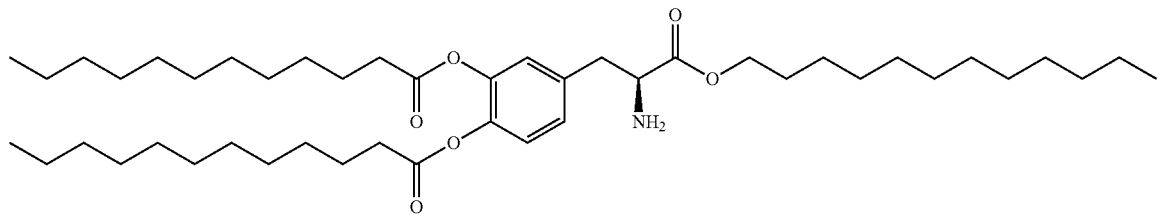 [SMILES: CCCCCCCCCCCCOC(=O)[C@@H](N)Cc1ccc(OC(=O)CCCCCCCCCCC)c(OC(=O)CCCCCCCCCCC)c1]

3. The compound according to claim 1, wherein the compound is an HCl salt having the following chemical formula:

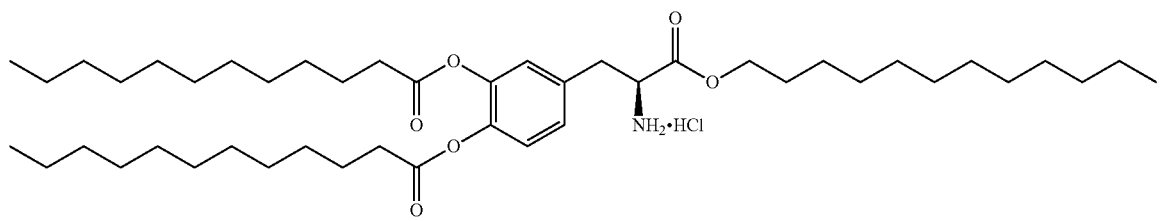

4. A composition comprising a pharmaceutically effective amount of the compound of claim 1 and one or more pharmaceutically acceptable carriers or excipients.

5. The composition of claim 4, wherein the composition is injectable, inhalable, orally ingestible, or topical.

6. The composition according to claim 4, wherein the composition is in the form of liposomes or micelles.

7. The composition according to claim 4, wherein the pharmaceutically acceptable carrier is castor oil or a derivative thereof.

* * * * *